United States Patent [19]

Le Guen et al.

[11] 4,180,510

[45] Dec. 25, 1979

[54] METHOD FOR PREPARING THIENYLACETIC ACIDS

[75] Inventors: Yves Le Guen, Cour Couronne; Georges Thiault, Nogent sur Marne, both of France

[73] Assignee: Produits Chimiques Auxiliaires et de Synthese, P.C.A.S., Paris, France

[21] Appl. No.: 868,909

[22] Filed: Jan. 12, 1978

[30] Foreign Application Priority Data

Jan. 12, 1977 [FR] France ............................... 77 00678

[51] Int. Cl.$^2$ .................. C07D 333/24; C07D 333/38
[52] U.S. Cl. ........................................ 549/79; 549/72
[58] Field of Search ......... 260/329 R, 332.8, 332.2 A, 260/332.2 C

[56] References Cited

PUBLICATIONS

Blicke et al., J.A.C.S., vol. 66, pp. 1645-1648 (1944).

Olah, editor, "Friedel-Crafts and Related Reactions" vol. 1, pp. 201 (1963).

Morrison & Boyd, "Organic Chemistry," 3rd Ed., pp. 625-627, 1008 (1973).

*Primary Examiner*—Gerald A. Schwartz
*Attorney, Agent, or Firm*—Oblon, Fisher, Spivak, McClelland & Maier

[57] ABSTRACT

A method for preparing thienylacetic acid and its derivatives is disclosed, wherein a glyoxylic ester is made to react with hydrazine, and after with potash. Advantageously, the glyoxylic ester is prepared by condensation of a monoester monochloride of oxalic acid upon a thiophenic derivative, in the presence of titanium chloride.

The so obtained products are useful as organic synthesis intermediaries for various products of pharmaceutical type.

4 Claims, No Drawings

METHOD FOR PREPARING THIENYLACETIC ACIDS

BACKGROUND OF THE INVENTION

This invention relates generally to a new method for preparing esters of thienylglyoxylic and thienylacetic acids.

Methods are known for a long time for preparing glyoxylic esters of thiophenic derivatives. Nevertheless, the results which were obtained were rather poor. Such methods are described, amongst others in: Bradley Ber, 19-2119 (1886), Steinkopf & Wolfram, Ann. 437,22 (1824), Blicke & Tsao, Jacs, 66, 1645 (1944), and more recently the French Pat. Nos. 2.068.425 (1969), 2.113.760 (1970) and 2.167.334 (1972).

In view of the increasing use of these products, such methods are too expensive and cannot allow the production of product with constant quality and with a sufficient yield.

STATEMENT OF THE INVENTION

It should be apparent, therefore, that a need exists in the art for a method for preparing thienylacetic acid and its derivatives, in good economic conditions, and with regular enough quality and properties.

According to the present invention, the glyoxylic esters are prepared by condensation of a monoester-monochloride of oxalic acid upon a thiophenic derivative, preferably in solution in a solvent of the methylenechloride type, in a manner known per se until there, but according to the present invention, in presence of titanium chloride TiCl4.

It was ascertained that with the use of titanium chloride as a catalyst, the yields were considerably increased, imparting to the method paying industrial possibilities, allowing to prepare thienylacetic acids in very favourable economic conditions.

Until now, the thienylacetic acids were prepared in three steps, namely:
(1) thiophene chloromethylation
(2) halogenated derivative cyaniding
(3) nitrile hydrolysis This method is explained in particular in: Blicke & Zienty, JACS, 63, 2945 (1941), Blicke & Leonard, JAC, 69, 1934, (1946).

According to the present invention, there is provided a method for the preparation of thienylacetic acid in which a glyoxylic ester is made to react with hydrazine, and after with potash.

For this reason, it is an object of the invention to provide a new method for the preparation of esters of α-thienylglyoxlic and thienylacetic acids.

It is another object of the invention to provide new compounds according to the following formulas:

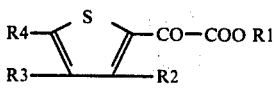  (a)

and

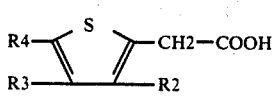  (b)

in which:

R1 is a lower alkyl radical of 1 to 5 carbon atoms;
R2, R3, R4 are either an hydrogen a lower alkyl radical, or a halogen (halogen only in formula a).

Compounds according to formula (a) are obtained by condensation of a monochloride-monoester of oxalic acid (such as methoxyalyle, ethoxyalyle, propioxalyle or butoxyalyle chloride) with a thiophenic derivative of general formula.

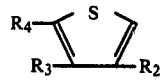

in which:
R2, R3, R4 are either hydrogen, a halogen, a lower alkyl radical with 1 to 5 carbon atoms, or an inferior alkyl radical and a halogen.

The condensation is made in a solvent of the type of methylene chloride or dichloro 1-2 ethane, and above all, in presence of titanium chloride (TiCl4).

After having stirred or agitated three hours at a temperature of 20° C., the reactant mixture is hydrolyzed on ice, decanted, washed with water, dried and distilled in vacuum. A yellow oil is obtained, which crystallises for some derivatives.

The compounds according to formula (b) are obtained with the foregoing glyoxylic ester which is made to react with hydrazine at a temperature of 100° C. over a period of about an hour, and after that with a potash solution in back-flow over a period of about six hours.

The compounds are isolated after acidification, extraction by an organic solvent such as methylene chloride, and finally recrystallised in hexane or heptane.

The glyoxylic ester yields are ranging about 80% and for thienylacetic acids, about 85%.

DESCRIPTION OF PREFERRED EMBODIMENTS

The present invention has principally for its object the thienylacetic acid which is prepared in the following manner:

EXAMPLE 1

Ethyl α-thienylglyoxylate

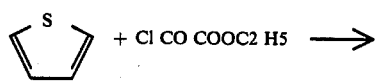

350 cm³ dried dichloromethane and 105 gr titanium chloride (Ti+4) are mixed under stirring. At a temperature of 20° C., 69 gr ethoxyalyle chloride are poured quickly, and after that 42 gr thiophene at a temperature between 0° and 5° C. is poured in the mixture.

The mixture as obtained is stirred during 4 hours at a temperature between 5° and 20° C. The mixture is then poured in 600 gr cold water. The lower organic solution is separated, washed with water unto neutrality, dried and distilled under vacuum.

78 gr of yellow oil (85%), distilling between 160° and 170° C. under 20 mm mercury (Hg) is obtained.

EXAMPLE 2

α-Thienylacetic acid

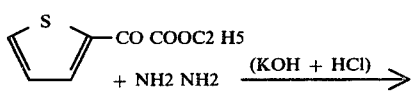

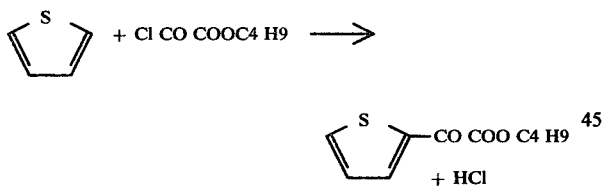

92 gr ethyl thienylglyoxylate and 26 gr hydrazine hydrate (98%) are introduced in a one liter threenecked flask. The temperature rises from 20° to 70° C. and hydrazone crystallises partially. The temperature is maintained at 90° C. during one hour with reflux. The temperature is lowered to 80° C. and 86 gr potash dissolved in 150 cm³ water is added. Heat is applied so as to maintain the temperature at 98°±2° C. in vapour whilst the condensate is collected.

Reflux is then maintained during six hours, then the temperature is lowered to 20° C. The mixture is poured on 400 gr ice and acidified with 150 cm³ concentrated hydrochloric acid.

Three times 100 cm³ methylene chloride is extracted; the organic phase is twice washed with 100 cm³ water, dried on Ca Cl2, thoroughly concentrated under vacuum and recrystallised in two volumes of hexane. 63 gr cream coloured flake crystals are collected, mp 60°–65° C., with an 88% yield.

EXAMPLE 3

Butyl-α-thienylglyoxylate

The condensation is made in the same conditions as in example 1, using butoxalyle chloride Cl CO (COO)4 H9 instead of ethoxyalyle chloride.

Yellow oil, bp: 170°–180° C. under 20 mm Hg—Yield 80%.

EXAMPLE 4

Methyl-α-thienylglyoxylate

Methoxalyl chloride is condensated in the same conditions.

Yellow oil, bp: 150°–160° C. under 20 mm Hg—Yield 70%.

The products obtained in examples 3 and 4 give thienylacetic acid when working thereafter as described in example 2.

The derivatives described below are obtained in an identical way.

EXAMPLE 5

Ethyl-methyl-2-thienyl-5-glyoxylate

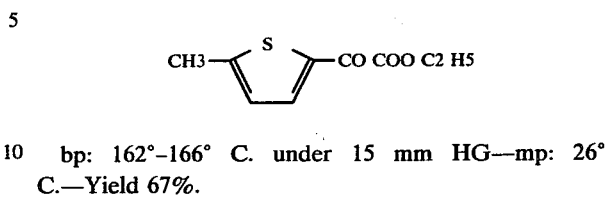

bp: 162°–166° C. under 15 mm HG—mp: 26° C.—Yield 67%.

EXAMPLE 6

Ethyl ethyl-2-thienyl-5-glyoxylate

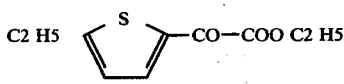

bp: 170° C. under 15 mm Hg—mp: 28° C.—Yield 70%.

EXAMPLE 7

Ethyl chloro-2-thienyl-5-glyoxylate

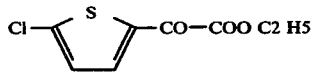

bp: 165° C. under 15 mm Hg—mp: 55° C.—Yield 65%.

EXAMPLE 8

Ethyl bromo-2-thienyl-5-glyoxylate

bp: 155°–158° C. under 10 mm Hg—mp: 30° C.—Yield 62%.

EXAMPLE 9

Ethyl bromo-3-thienyl-2-glyoxylate

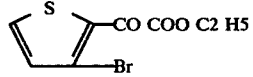

bp: 185°–190° C. under 16 mm Hg—mp: 68° C.—Yield 67%.

EXAMPLE 10

Ethyl chloro-3-thienyl-2-glyoxylate

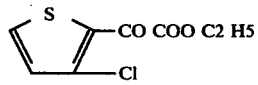

bp: 165° C. under 15 mm Hg—mp: 25° C.—Yield 70%.

EXAMPLE 11

Ethyl methyl-3-thienyl-2-glyoxylate

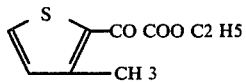

bp: 160° C. under 15 mm Hg—mp: 38° C.—Yield 68%.

EXAMPLE 12

Propyl methyl-3-thienyl-2-glyoxylate

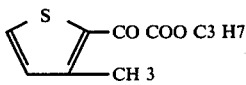

bp: 170°–173° C. under 15 mm Hg—mp: 48° C.—Yield 70%.

EXAMPLE 13

Butyl bromo-3-thienyl-2-glyoxylate

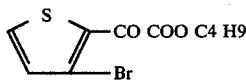

bp: 180°–190° C. under 5 mm Hg—mp: 75° C.—Yield 62%.

EXAMPLE 14

Methyl chloro-2-thienyl-5-glyoxylate

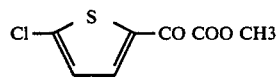

bp: 165° C. under 15 mm Hg—Yield 71%.

EXAMPLE 15

Methyl methyl-2-thienyl-5-glyoxylate

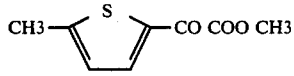

bp: 162°–165° C. under 10 mm Hg—Yield 73%.

EXAMPLE 16

Methyl-3-thienyl-2 acetic acid

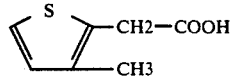

bp: 158° C. under 15 mm Hg—mp: 92°–93° C.—Yield 82%.

EXAMPLE 17

Methyl-5-thienyl-2 acetic acid

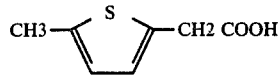

mp: 56° C.—Yield 87%.

EXAMPLE 18

Ethyl-5-thienyl-2 acetic acid

bp: 165° C. under 15 mm Hg—$n_{16}^D$: 1,5340—Yield 98%.

Although preferred embodiments are specifically described herein, it will be appreciated that many modifications and variations of the present invention are possible in light of the above teachings and within the purview of the appended claims without departing from the spirit and intended scope of the invention.

We claim:

1. A method for the preparation of α-thienylacetic acid comprising:

condensing a thiophene compound of the formula:

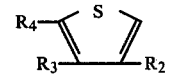

wherein $R_2$, $R_3$ and $R_4$ are each hydrogen, halogen, or lower alkyl of 1 to 5 carbon atoms or are each lower alkyl or halogen, with a monochloride-monoester of oxalic acid in a solvent of methylene chloride or 1,2-dichloroethane in the presence of titanium tetrachloride, thereby forming a glyoxalic acid ester of the formula:

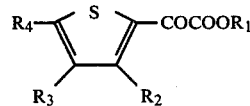

wherein $R_1$ is lower alkyl of 1 to 5 carbon atoms and $R_2$, $R_3$ and $R_4$ are as defined above; and forming said α-thienylacetic acid by reducing said glyoxalic acid ester with hydrazine; and thereafter reacting said reduced ester obtained with an aqueous potash solution.

2. The method of claim 1, wherein said condensation reaction is conducted for 3 hours with stirring at a temperature of 20° C. and thereafter the mixture obtained is hydrolyzed on ice, washed with water, dried and distilled under vacuum.

3. The method of claim 1, wherein said reaction of said ester with said hydrazine is conducted for an hour at a temperature of 100° C., and thereafter the mixture is reacted for about 6 hours with an aqueous potash solution under reflux conditions and the product isolated after an acidification is extracted with methylene chloride and finally recrystallized from hexane or heptane.

4. The method of claim 2, wherein said monochloride-monoester of oxalic acid is methoxalyl, ethoxalyl, propoxalyl or butoxalyl chloride.

* * * * *